(12) United States Patent
Dinkler, II

(10) Patent No.: US 8,287,537 B2
(45) Date of Patent: Oct. 16, 2012

(54) HEAD FIXATION DEVICE

(75) Inventor: Charles E. Dinkler, II, Dayton, OH (US)

(73) Assignee: Dinkler Surgical Devices, Inc., Dayton, OH (US)

( * ) Notice: Subject to any disclaimer, the term of this patent is extended or adjusted under 35 U.S.C. 154(b) by 202 days.

(21) Appl. No.: 12/478,103

(22) Filed: Jun. 4, 2009

(65) Prior Publication Data

US 2009/0306662 A1 Dec. 10, 2009

Related U.S. Application Data

(60) Provisional application No. 61/058,939, filed on Jun. 5, 2008.

(51) Int. Cl.
*A61B 17/00* (2006.01)

(52) U.S. Cl. ............................ 606/59; 606/56

(58) Field of Classification Search ............... 606/54–59
See application file for complete search history.

(56) References Cited

U.S. PATENT DOCUMENTS

| | | | |
|---|---|---|---|
| 4,051,918 A * | 10/1977 | Rogers | 181/119 |
| 4,108,426 A | 8/1978 | Lindstroem et al. | |
| 4,252,149 A * | 2/1981 | Dollison | 137/625.44 |
| 4,360,028 A | 11/1982 | Barbier et al. | |
| 4,545,572 A | 10/1985 | Day | |
| 4,575,443 A * | 3/1986 | Moen et al. | 264/161 |
| 5,147,287 A | 9/1992 | Jewell et al. | |
| 5,537,704 A | 7/1996 | Dinkler | |
| 5,954,466 A * | 9/1999 | Coffey et al. | 411/119 |
| 6,117,143 A * | 9/2000 | Hynes et al. | 606/130 |
| 6,179,846 B1 | 1/2001 | McFadden et al. | |
| 6,315,783 B1 | 11/2001 | Katz et al. | |
| 6,629,982 B2 | 10/2003 | Day et al. | |
| 6,684,428 B2 | 2/2004 | Grotenhuis et al. | |
| 6,770,082 B2 | 8/2004 | Dominguez et al. | |
| 2001/0051806 A1* | 12/2001 | Ballier | 606/54 |
| 2004/0097985 A1 | 5/2004 | Day et al. | |
| 2005/0251136 A1* | 11/2005 | Noon et al. | 606/56 |
| 2007/0250071 A1 | 10/2007 | Soerensen et al. | |

OTHER PUBLICATIONS

International Search Report and Written Opinion pertaining to International application No. PCT/US2009/046212 dated Jan. 19, 2010.

* cited by examiner

*Primary Examiner* — Eduardo C Robert
*Assistant Examiner* — Stuart S Bray
(74) *Attorney, Agent, or Firm* — Daniel F. Nesbitt; Hasse & Nesbitt LLC

(57) ABSTRACT

Head fixation devices and methods of fixating heads of patients for surgical procedures. The head fixation devices generally respectively comprise a skull clamp, a skull clamp arc assembly movable relative to the skull clamp, and a plurality of skull pins operable to engage and fixate heads of patients during neurosurgical and cervical spine procedures. The skull clamp can comprise a single skull pin on each end of the clamp. The two skull pins apply substantially equal compressive forces to the head of a patient. The skull clamp arc assembly, and an arc skull pin thereof, is pivotable to engage and disengage the patient's head for additional fixation support of the head.

18 Claims, 10 Drawing Sheets

HEAD FIXATION DEVICE

CROSS-REFERENCE TO RELATED APPLICATIONS

This application claims the benefit of U.S. Provisional Application Ser. No. 61/058,939, filed Jun. 5, 2008.

BACKGROUND

Embodiments of the present disclosure relate generally to head fixation devices for use with surgical head frames during surgical procedures. More particularly, the embodiments relate to head fixation devices respectively comprising a skull clamp, a skull clamp arc assembly movable relative to the skull clamp, and a plurality of skull pins to engage and fixate heads of patients during surgical procedures.

Conventional three pin, C-shaped skull clamps typically are used with surgical head fixation devices to support a head of a patient during neurosurgical and cervical spine procedures. The skull clamp works like a C-clamp, or vise, to keep the head of the patient steady as surgeries are performed. Typically, on one side of the skull clamp is a rocker arm containing two skull pins and on the opposing side is a mechanism to engage and advance a third pin into the skull of the patient. Between about sixty pounds and about eighty pounds of compressive force typically are applied to the head with the third skull pin. It is then customary to assume that, as the third skull pin is driven into the skull, each of the rocker arm skull pins will apply approximately half of the force being applied by the third pin, or between about thirty pounds and about forty pounds of compressive force, to the head of an adult patient if the skull clamp is properly positioned and applied on the patient's head.

However, problems may arise if the rocker arm skull pins are not properly positioned or applied to the head. For example, if the rocker arm is not aligned properly with the third pin, the compressive force applied by each of the two rocker arm skull pins may not be equal. This inequity in applied compressive forces could negatively effect the ability of the conventional skull clamp to fixate the head of the patient. Additionally, if the rocker arm is misaligned with the third skull pin, the rocker arm skull pins may not apply an appropriate compressive force, thereby potentially resulting in rotation of the patient's head during a surgical procedure and/or in slippage of the skull pins along the head, which may cause injurious skin and tissue tears on the head.

As such, based on the foregoing, there exists a need for a head fixation device comprising a skull clamp and at least two opposing skull pins positioned such that they apply substantially equal compressive forces to each side of the head and at least one movable arc skull pin offset from the opposing skull pins to engage and further fixate a patient's head during a surgical procedure.

SUMMARY

It is against the above background that embodiments of the present disclosure generally relate to head fixation devices that respectively comprise a skull clamp, a skull clamp arc assembly movable relative to the skull clamp, and a plurality of skull pins to engage and fixate heads of patients during neurosurgical and cervical spine procedures. The skull clamp comprises at least one skull pin on each end of the clamp. The two skull pins apply substantially equal compressive forces to the head of a patient. The skull clamp arc assembly, and an arc skull pin thereof, is pivotable to engage and disengage the patient's head for additional fixation support of the head.

In accordance with one embodiment, a head fixation device comprises a skull clamp, a first skull pin, a second skull pin, and a skull clamp arc assembly. The skull clamp is positionable about a head of a patient and comprises a first end and a second end opposing the first end. The first skull pin is provided to the first end of the skull clamp and the second skull pin is provided to the second end of the skull clamp, wherein the first and second skull pins are aligned in opposition along an axis. At least one of the first and second skull pins is movable relative to the first and second ends such that the first and second skull pins engage and disengage the head of the patient when the skull clamp is positioned thereabout. The skull clamp arc assembly comprises an arc skull pin and extends from one of the first and second ends of the skull clamp such that the arc skull pin is offset from the axis. The skull clamp arc assembly is movable relative to the first and second ends of the skull clamp such that the arc skull pin is operable to engage and disengage the head of the patient with movement of the skull clamp arc assembly.

In accordance with another embodiment, the skull clamp arc assembly of the head fixation device is rotatable relative to the one of the first and second ends from which the skull clamp arc assembly extends such that the skull clamp arc assembly rotates about the horizontal axis defining the axis. In addition, the skull clamp arc assembly is pivotable relative to the one of the first and second ends such that the arc skull pin pivots toward and away from the horizontal axis defining the axis.

In accordance with yet another embodiment, a method of fixating a head of a patient comprises providing a head fixation device operable to fixate the head of the patient. The head fixation device comprises: a skull clamp comprising a first end and a second end opposing the first end, a first skull pin provided to the first end of the skull clamp and a second skull pin provided to the second end of the skull clamp, wherein the first and second skull pins are aligned in opposition along an axis, and a skull clamp arc assembly comprising an arc skull pin. The skull clamp arc assembly extends from one of the first and second ends of the skull clamp such that the arc skull pin is offset from the axis. The method further comprises positioning the head fixation device about the head of the patient such that the first and second ends of the skull clamp are positioned about the head of the patient. Thereafter, the method comprises moving at least one of the first and second skull pins relative to the first and second ends of the skull clamp such that the first and second skull pins engage the first and second sides of the head of the patient and rotating the skull clamp arc assembly relative to the first and second ends such that the skull clamp arc assembly rotates about the axis to selectively position the arc skull pin over a third side of the head of the patient. In addition, the method comprises pivoting the skull clamp arc assembly relative to the first and second ends such that the arc skull pin pivots to engage the third side of the head of the patient. The engagements of the first, second, and third sides of the head of the patient by the first skull pin, the second skull pin, and the arc skull pin, respectively, sufficiently fixate the head of the patient.

BRIEF DESCRIPTION OF THE DRAWINGS

The following detailed description of specific embodiments can be best understood when read in conjunction with the following drawings, where like structure is indicated with like reference numerals and in which.

Figure 1A:
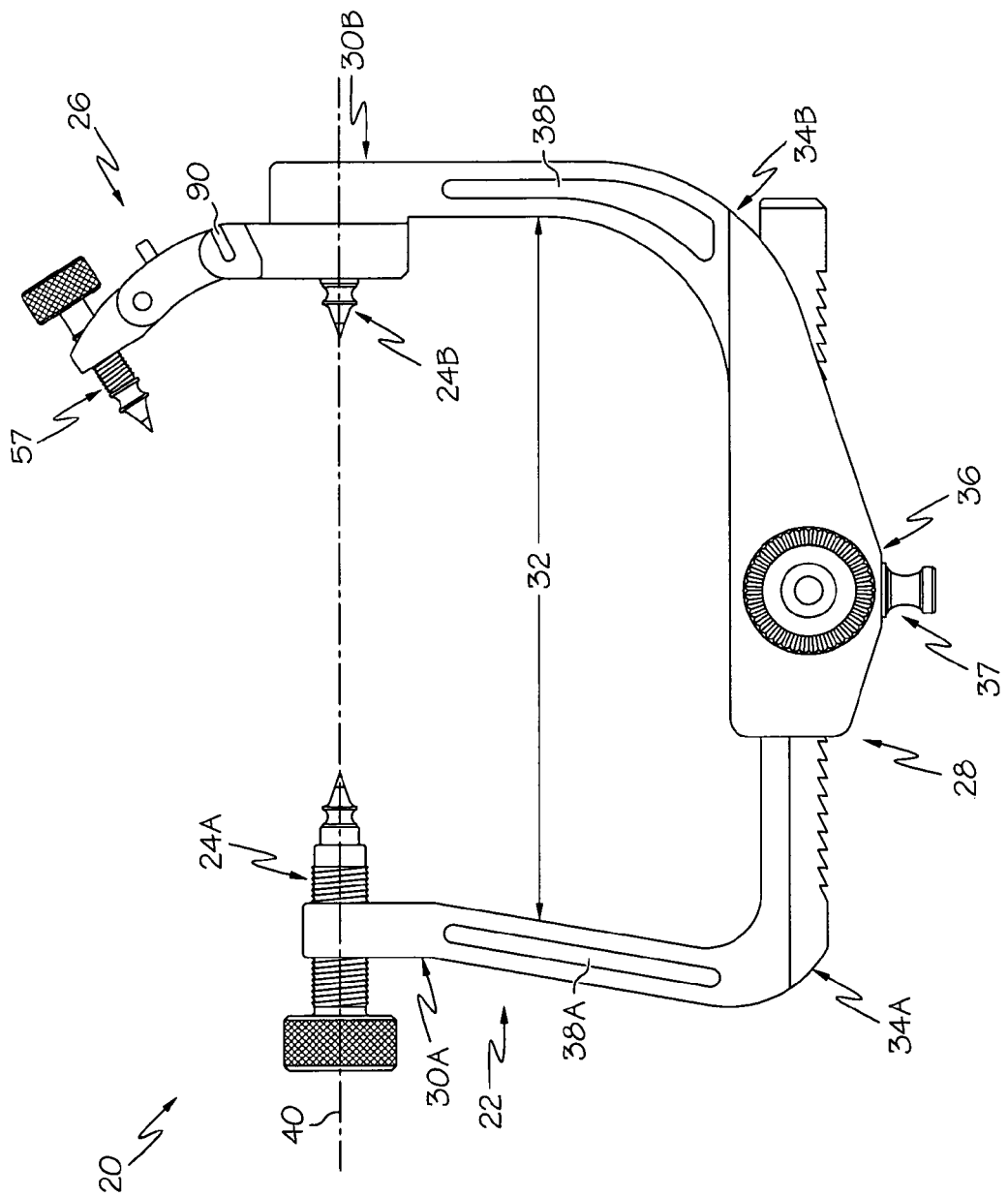
FIG. 1A illustrates a frontal view of a head fixation device according to one embodiment of the present disclosure.

The embodiments set forth in the drawings are illustrative in nature and are not intended to be limiting of the embodiments defined by the claims. Moreover, individual aspects of the drawings and the embodiments will be more fully apparent and understood in view of the detailed description that follows.

DETAILED DESCRIPTION

Referring initially to FIG. 1A, a head fixation device 20 comprises a skull clamp 22, a first skull pin 24A and a second skull pin 24B, and a skull clamp assembly 26 that extends from the skull clamp 22. The skull clamp 22 is positionable about a head of a patient. The skull clamp 22 generally, but not necessarily, comprises a C-clamp-like shape including a body 28, a first end 30A, and a second end 30B opposing the first end 30A. It also is contemplated that the skull clamp 22 may comprise a circular, oval, polygonal, or other shape that may be configured to function as disclosed herein or otherwise inferable there-from.

The first and second ends 30A, 30B of the C-clamp-like shape skull clamp 22 are separated by a gap 32 sufficient to accommodate the head of a child or adult patient. The body 28 of the skull clamp 22 may comprise two complementary ratcheting arms 34A, 34B. The ratcheting arms 34A, 34B may be operable to move relative to one another via a shared ratcheting mechanism 36 to adjust the length of the gap 32 separating the first and second ends 30A, 30B of the skull clamp 22. The ratcheting mechanism 36 may comprise a spring-biased pin 37 to control a locking and unlocking of the ratcheting arms 34A, 34B to preclude and permit, respectively, lateral movement thereof. The ratcheting arms 34A, 34B may comprise grip areas 38A, 38B designed to facilitate a user's gripping of the ratcheting arms 34A, 34B to adjust the length of the gap 32. It also is contemplated that one or more mechanisms in addition to or in the alternative of the ratcheting mechanism 36 may be used to permit and control adjustment of the length of the gap 32 separating the first and second ends 30A, 30B.

The first and second skull pins 24A, 24B are provided to the first and second ends 30A, 30B, respectively, and, as such, are separated by the gap 32. Thereby, the first and second skull pins 24A, 24B move closer together and farther apart in accordance with the movement of the skull clamp body 28, whether via the ratcheting mechanism 36 or otherwise. In addition, the first and second skull pins 24A, 24B are aligned in opposition along an axis 40. As used herein, "aligned in opposition along an/the axis" refers generally to at least a respective portion of the first and second skull pins 24A, 24B being substantially aligned along a line and is not intended to imply that the pins 24A, 24B, when engaged with the head of a patient, are necessarily applied to directly opposite points on the head. As such, it is contemplated that not only may the first and second pins 24A, 24B be parallel, or substantially parallel, but also that portions of the skull pins 24A, 24B may be offset from one another at an angle, whether acutely or obtusely, or otherwise, wherein at least a respective portion of the offset skull pins, such as respective skull-engaging tips thereof, remain substantially aligned along the line.

Further, at least one of the first and second skull pins 24A, 24B may be movable relative to, and independent of, the first and second ends 30A, 30B of the skull clamp 22 so as to engage and disengage the head of the patient when the skull clamp 22 is positioned thereabout. More particularly, the skull pins 24A, 24B individually may comprise a tip 42 secured to the first and second ends 30A, 30B, as shown in FIG. 1A with respect to the second skull pin 24B, and operable to engage the head of a patient. Alternatively, as shown in FIG. 1A with respect to the first skull pin 24A and in greater detail in FIGS. 4 and 9, the skull pins 24A/24A", 24B/24B" individually may comprise, in addition to the tip 42, a plunger 44/44", a plunger guide 46/46", and a compression spring 48/48" that may cooperate to permit lateral movement of the skull pins 24A/24A", 24B/24B" along the axis 40 relative to, and independent of, the first and second ends 30A, 30B of the skull clamp 22. The plunger 44 may be operable to support the tip 42, while the plunger guide 46 may be operable to control movement of the plunger 44 and the tip 42. The compression spring 48 may be operable to translate movement of the plunger guide 46 to the plunger 44 and the tip 42, whether that movement be toward the opposing skull pin or away therefrom. The tip 42, whether secured to the first or second end 30A, 30B or supported by the plunger 44, may be removed from the head fixation device 20 and discarded as a disposable component of the device 20 and, thereafter, replaced with another tip 42.

Figure 4:
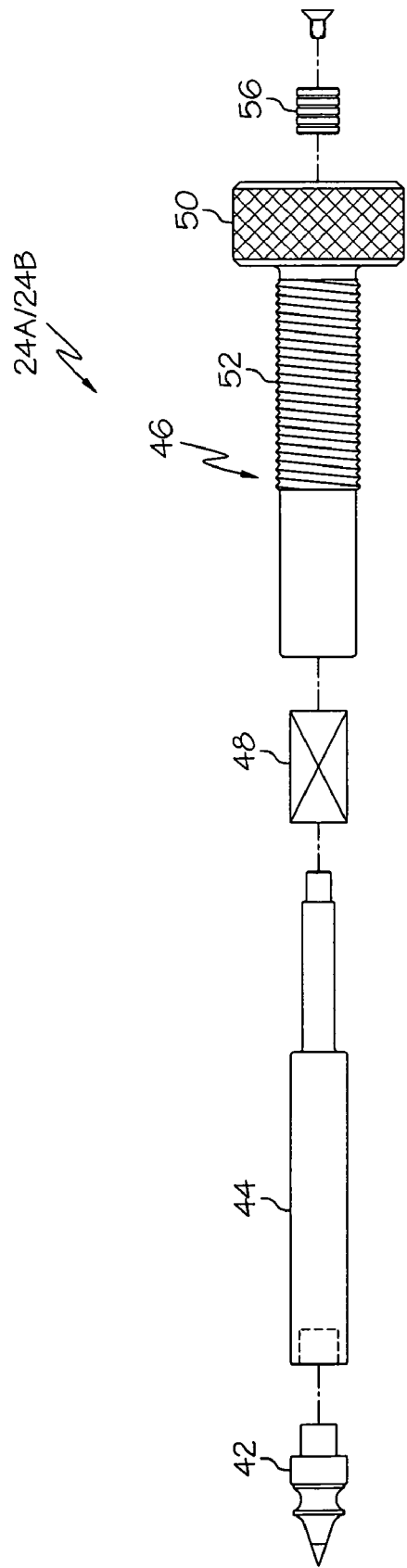
FIG. 4 illustrates a cross-sectional view of a skull pin according to another embodiment of the present disclosure.
Figure 5:
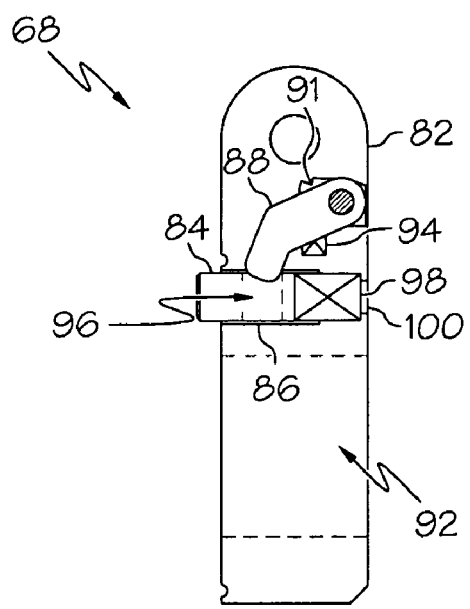
FIG. 5 illustrates a cross-sectional view of a rocker guide assembly of a head fixation device according to another embodiment of the present disclosure.
Figure 9:
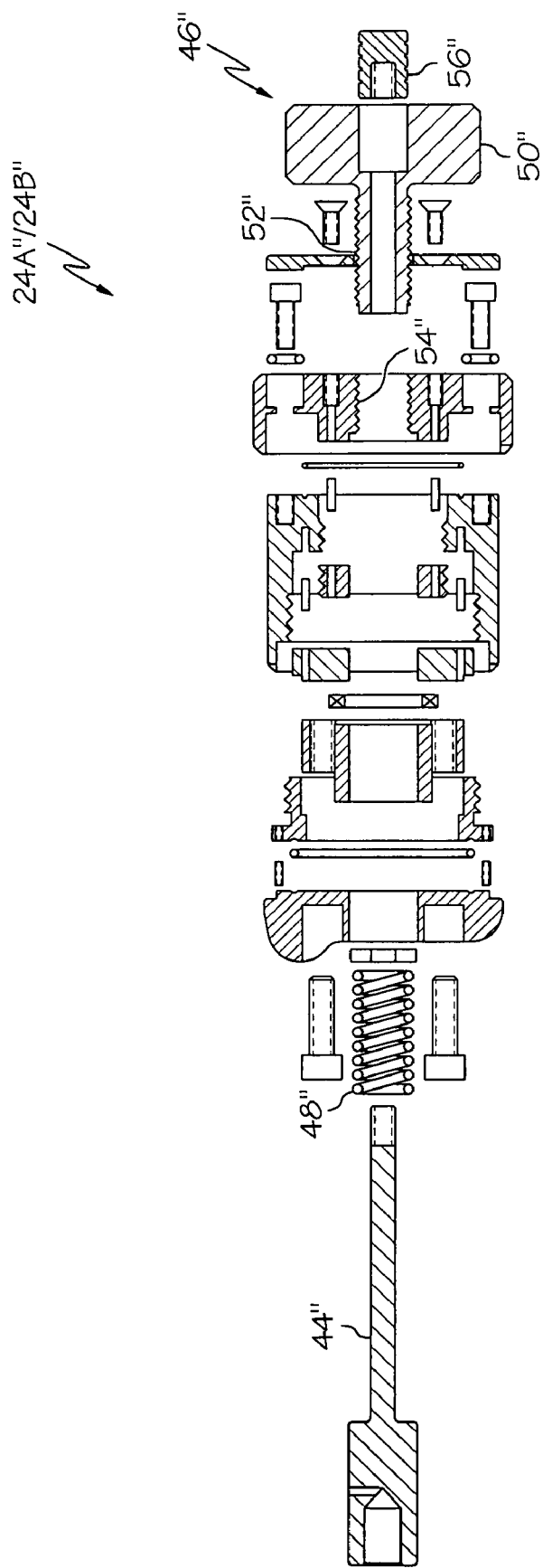
FIG. 9 illustrates an exploded view of a skull pin assembly of the head fixation device illustrated in FIG. 8.

As shown in FIGS. 4 and 9, the plunger guide 46/46" may comprise a knob 50/50" and a threaded exterior surface 52/52" that may complement a threaded interior channel 54/54" of the first and/or second end 30A, 30B through which the skull pin 24A/24A", 24B/24B" may pass. Rotation of the knob 50 by a user of the device 20 may advance or withdraw the skull pins 24A, 24B through the first and second ends 30A, 30B of the skull clamp 22. For example, a compressive direction of rotation applied to the knob 50 of the first skull pin 24A may advance the plunger guide 46 through the first end 30A to contract the compression spring 48, which may advance the plunger 44 and the first skull pin 24A toward the second skull pin 24B. Thereby, with such advancement, the first skull pin 24A may engage and apply an increasing compressive force against the head of the patient when the skull clamp 22 is positioned thereabout. Conversely, for example, a decompressive direction of rotation applied to the knob 50 of the first skull pin 24A may draw the plunger guide 46 through the first end 30A to extend the compression spring 48, which may draw the plunger 44 and the first skull pin 24A away from the second skull pin 24B. Thereby, with such withdrawal, the first skull pin 24A may gradually reduce the compressive force applied against the head of the patient and, eventually, disengage the head. The skull pins 24A/24A", 24B/24B" respectively may comprise an indicator 56/56" operable to indicate the compressive force applied by the respective tip 42 against the head of a patient when the skull clamp 22 is positioned thereabout.

It is contemplated that, regardless of the respective configurations of the first and second skull pins 24A, 24B, the skull pins 24A, 24B are positioned on the skull clamp 22 so that they are operable to apply substantially equal compressive forces against the head of the patient when engaged therewith. Thereby, the head fixation device 20 substantially fixates the head of a patient when engaged therewith and, when used in cooperation with the arc skull pin 57, minimizes the potential for rotation of the head and for slippage of the skull pins 24A, 24B along the head.

In addition to the first and second skull pins 24A, 24B provided to the skull clamp 22, the skull clamp arc assembly 26 comprises a skull pin 57, referred to herein as the arc skull pin 57. As shown in FIG. 1A, the skull clamp arc assembly 26 extends from at least one of the first and second ends 30A, 30B of the skull clamp 22. Thereby, the arc skull pin 57 is offset from the axis 40 and the first and second skull pins 24A, 24B.

Figure 3:
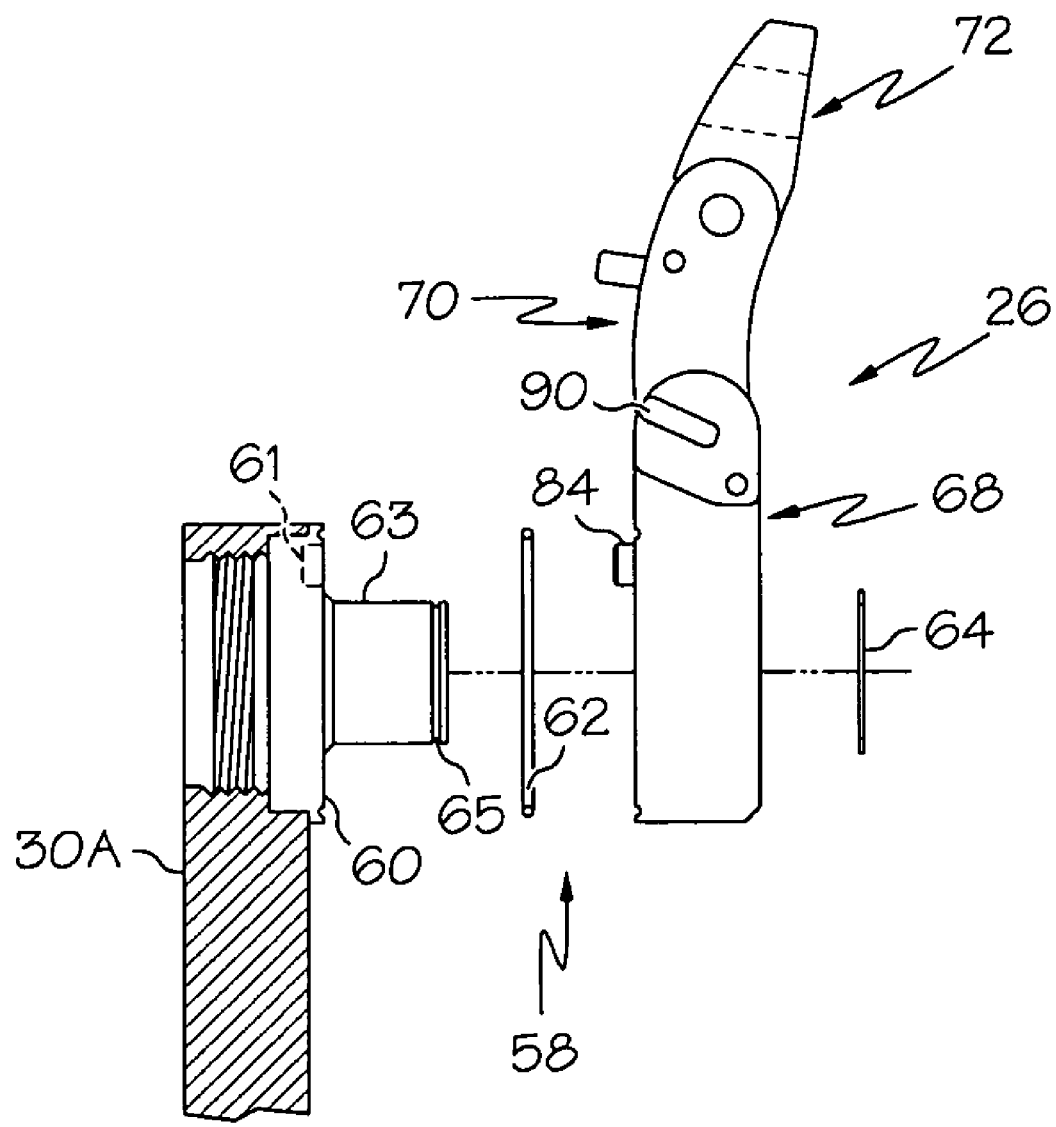
FIG. 3 illustrates a view of a skull clamp arc assembly and a locking assembly of a head fixation device according to another embodiment of the present disclosure.

As shown in FIG. 3, the skull clamp 22 generally comprises a locking assembly 58 provided at the first and/or second end 30A, 30B from which the skull clamp arc assembly 26 extends. The locking assembly 58 is operable to secure the skull clamp arc assembly 26 to the first or second end 30A, 30B. The locking assembly 58 may comprise any variety of one or more components and/or mechanisms to function as described herein. In one embodiment, shown in FIG. 3, the locking assembly 58 comprises a locking plate 60, an o-ring 62, and a snap ring 64. The locking plate 60 may be operable to secure immovably to the first or second end 30A, 30B of the skull clamp 22 and to support the skull clamp arc assembly 26. The locking plate 60 may comprise at least one recess 61 into which a locking pin 84 may insert to prevent movement of the skull clamp arc assembly 26 relative thereto, as described in greater detail below. The locking plate 60 also generally comprises a post 63 and a depression 65 provided proximally to the end of the post 63. The o-ring 62 is positionable about the post 63 and may be operable to facilitate movement of the skull clamp arc assembly 26 relative to the locking plate 60 and the first or second end 30A, 30B. The snap ring 64 may be operable to secure the skull clamp arc assembly 26 to the locking plate 60 by snapping or otherwise securing to the depression 65 in the post 63 of the locking plate 60.

The skull clamp arc assembly 26 is movable relative to first or second end 30A, 30B from which it extends such that the arc skull pin 57 is operable to engage and disengage the head of a patient with movement of the skull clamp arc assembly 26. For example, in one embodiment, the skull clamp arc assembly 26 is rotatable relative to the first or second end 30A, 30B such that the skull clamp arc assembly 26 rotates about the axis 40.

Figure 1B:
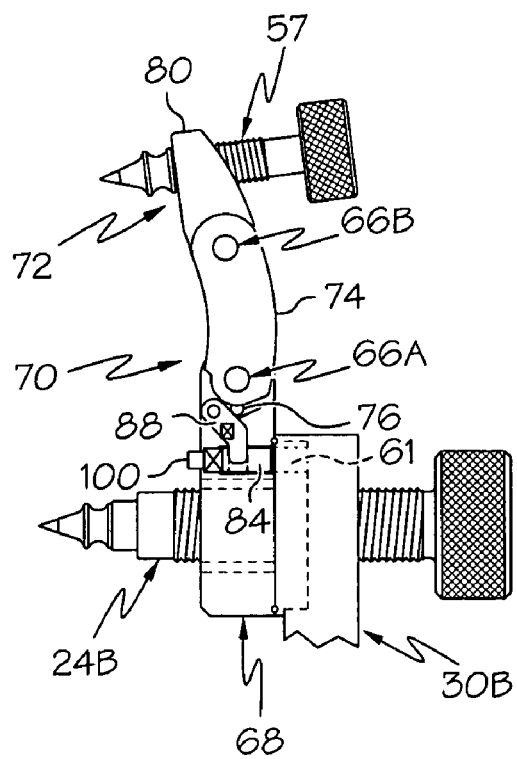
FIG. 1B illustrates a magnified view of a skull clamp arc assembly of a head fixation device according to the embodiment of the present disclosure illustrated in FIG. 1A where the skull clamp arc assembly is pivoted to a maximum pivot away from the axis along which first and second skull pins are aligned.
Figure 1C:
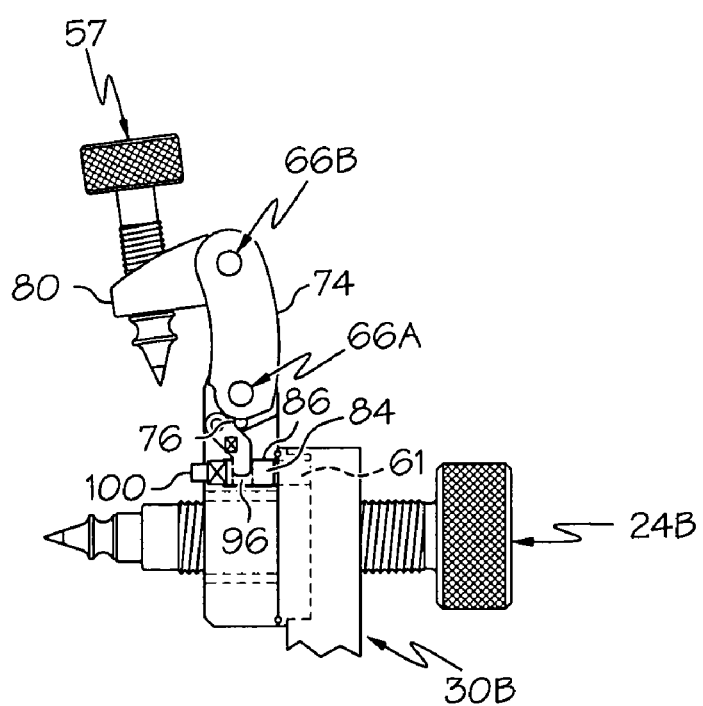
FIG. 1C illustrates a magnified view of a skull clamp arc assembly of the head fixation device illustrated in FIG. 1A where the skull clamp arc assembly is pivoted toward the axis along which first and second skull pins are aligned.

In addition thereto, or in the alternative thereof, the skull clamp arc assembly 26 may be pivotable relative to the first or second end 30A, 30B from which it extends such that the arc skull pin 57 may pivot toward and away from the axis 40. Thereby, the arc skull pin 57 may engage and disengage the head of a patient when the skull clamp 22 is positioned thereabout. For example, as shown in FIGS. 1B and 1C, the skull clamp arc assembly 26 may comprise a plurality of pivot points, whether two or more, pivot points 66A, 66B, such that the arc skull pin is pivotable relative to the first and second ends 30A, 30B and the axis 40. Thus, by virtue of at least one of the rotational and pivotal movements of the skull clamp arc assembly, the arc skull pin 57 may be selectively positioned as desired. Further, where the skull clamp arc assembly 26 is both rotatable and pivotable relative to the first or second end 30A, 30B from which it extends, as described above, to minimize potential for inadvertent rotational movement of the arc skull pin 57 along the head of a patient, the skull clamp arc assembly 26 may be configured such that it is rotatable only with a pivoting of the skull clamp arc assembly 26 about at least one of the pivot points 66A, 66B to a maximum pivot away from the axis 40.

The skull clamp arc assembly 26 may comprise one of any variety of configurations comprising one or more of any variety of components and/or mechanisms suitable to enable the assembly 26 to function as described herein. In one embodiment, shown in FIGS. 1B, 1C, and 3, the skull clamp arc assembly 26 comprises a rocker guide assembly 68, a lower rocker assembly 70, and an upper rocker assembly 72. The rocker guide assembly 68 is securable to the one of the first and second ends 30A, 30B from which the skull clamp arc assembly 26 extends. Further, the lower rocker assembly 70 is securable to the rocker guide assembly 68 at the first pivot point 66A, while the upper rocker assembly 72 is securable to the lower rocker assembly 70 at the second pivot point 66B. The lower rocker assembly 70 is pivotable about the first pivot point 66A toward and away from the axis 40, while the upper rocker assembly 72 is pivotable about the second pivot point 66B toward and away from the axis 40.

Figure 6A:
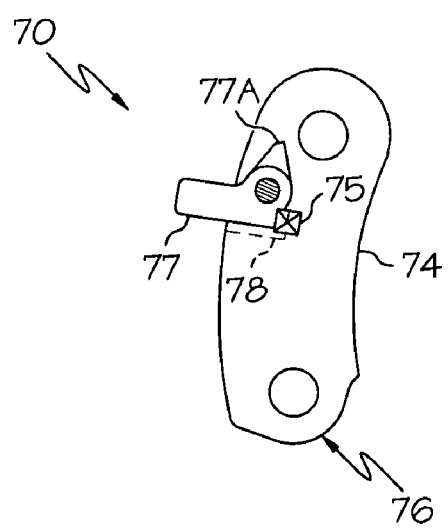
FIG. 6A illustrates a cross-sectional view of a lower rocker assembly of a head fixation device according to another embodiment of the present disclosure.
Figure 6B:
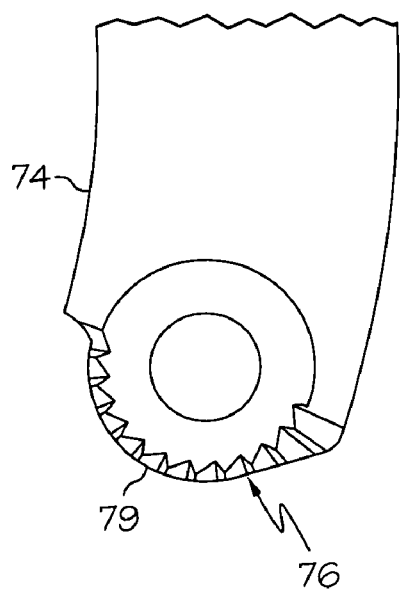
FIGS. 6B and 6C illustrate a frontal view and a side view, respectively, of a lower rocker assembly comprising a ratcheted configuration of a head fixation device according to another embodiment of the present disclosure.
Figure 6C:
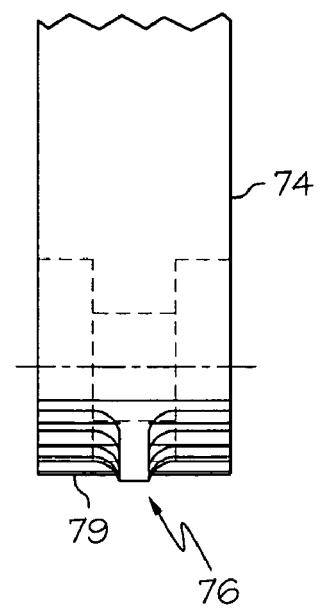

As shown in FIG. 6, the lower rocker assembly 70 may comprise a lower rocker arc 74, a cam 76, a pawl lever 77, and a recess 78 in the lower rocker arc 74 at least partially housing the pawl lever 77. The lower rocker assembly 70 may be locked and unlocked, via a ratchet configuration or otherwise, by a user of the head fixation device 20 to preclude and permit, respectively, pivoting of the lower rocker assembly 70 about the first pivot point 66A. More particularly, the cam 76 may comprise a grooved portion 79 that engages a ratchet 91 of the rocker guide assembly 68. The ratchet 91 may be spring-biased such that with depression of a pawl 90 of the rocker guide assembly 68 by a user of the device 20, the ratchet 91 disengages the grooved portion 79 of the cam 76, thereby enabling pivoting of the cam 76 and, thus, the lower rocker arc 74, relative to the rocker guide assembly 68. When the lower rocker arc 74 is positioned as desired, the user may release the pawl 90 of the rocker guide assembly 68. The biasing spring thereby transitions the ratchet 91 to engage the grooved portion 79 of the cam 76, locking it in place.

Figure 7A:
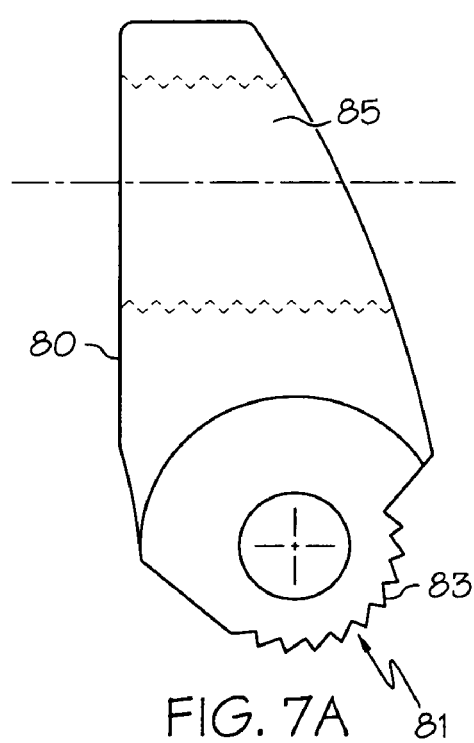
FIGS. 7A and 7B illustrate a frontal view and a side view, respectively, of an upper rocker assembly comprising a ratcheted configuration of a head fixation device according to another embodiment of the present disclosure.
Figure 7B:
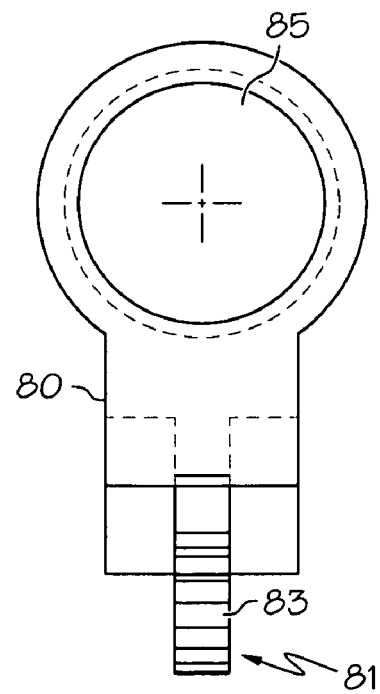

The upper rocker assembly 72 may comprise an upper rocker arc 80 and a cam 81, as shown in FIG. 7. The pawl lever 77 of the lower rocker assembly 70 may be actuated by the user to unlock the upper rocker arc 80 of the upper rocker assembly 72 so that it is pivotable about the second pivot point 66B. Also, the pawl lever 77 may be actuated to lock the upper rocker arc 80 so that the upper rocker assembly 72 is not pivotable about the second pivot point 66B. For example, the pawl lever 77 may be spring-biased by a pawl lever spring 75 and comprise a projection 77A operable to lock and unlock the upper rocker assembly 72 so as to preclude and permit, respectively, movement thereof. The spring-biased pawl lever 77 may be depressed by a user to pivot the projection 77A away from, and thereby disengage, the cam 81 of the upper rocker assembly 72 so that the upper rocker arc 80 may pivot toward and away from the axis 40. Upon the user's release of the spring-biased pawl lever 77, the lever 77 may transition to its relaxed state so that the projection 77A pivots toward, and thereby engages, the cam 81 so that the upper rocker arc 80 assumes a locked state and is precluded from pivoting. The cam 81 may comprise a grooved portion 83 that may be engaged and disengaged by the projection 77A to prevent and enable, respectively, a ratcheted movement of the cam 81 and, thus, the upper rocker arc 80, relative to the lower rocker assembly 70.

Also, the upper rocker arc 80 may be operable to receive and support the arc skull pin 57 in the channel 85 extending at least partially through the arc 80. Thereby, the arc skull pin 57 may be operable to engage and disengage the head of a patient with pivoting of the upper rocker arc 80 about the second pivot point 66B toward and away from the axis 40. Further, as described herein with respect to the first and second skull pins 24A, 24B, the arc skull pin 57 may be movable independently of and relative to the upper rocker arc 80 in which the arc skull pin 57 is supported so as to move toward and away from the axis 40. For example, the arc skull 57 may comprise a tip secured to the upper rocker 80 or, in addition to the tip, may comprise a plunger, a plunger guide, and a compression spring that may cooperate to move the tip relative to the upper rocker arc 80.

As shown in FIGS. 1B, 1C, 3, and 5, the rocker guide assembly 68 is securable to the post 63 of the locking plate 60 provided to the one of the first and second ends 30A, 30B of the skull clamp 22 and may be rotatable relative to the first or second end 30A, 30B such the skull clamp arc assembly 26 may rotate about the axis 40. Such rotation of the skull clamp arc assembly 26 may be restricted to a pivoting of at least one of the lower rocker assembly 70 and the upper rocker assembly 72 about the first pivot point 66A and the second pivot point 66B, respectively, to a respective maximum pivot away from the axis 40.

In one embodiment, the rocker guide assembly 68 may comprise a body 82, a locking pin 84, a recess 86 in the body 82 at least partially housing the locking pin 84, a locking lever 88, a pawl 90, a ratchet 91, and a channel 92 through the body 82 through which the rocker guide assembly 68 is securable to the post 63 of the locking plate 60. The rocker guide assembly 68 may be operable such that, as described above, with depression of the pawl 90, a ratchet 91 releases from an engagement with the cam 76 of the lower rocker assembly 70, thereby permitting it to pivot about the first pivot point 66A. The user may pivot the lower rocker assembly 70 until a desired position thereof is attained, at which time the user may release the pawl 90 from the depression, which allows a spring 94 to bias the ratchet 91 to engage the cam 76 and lock it in position and to advance the pawl 90 to its projected state. As the lower rocker assembly 70 pivots to a maximum pivot away from the axis 40, the cam 76 of the lower rocker assembly 70 engages the locking lever 88 of the rocker guide assembly 68. With engagement thereof, the locking lever 88 transitions the locking pin 84 from a locked state to an unlocked state so that the skull clamp arc assembly 26 is rotatable relative to locking plate 60 and the first or second end 30A, 30B from which it extends. As such, the skull clamp arc assembly 26 may rotate about the axis 40.

More particularly, in one embodiment, the locking pin 84 is biased with a spring 98 to a locked state in which the locking pin 84 is inserted into one of the recesses 61 in the locking plate 60, as shown in FIGS. 1B, 1C, 3, and 5. It is contemplated that any number of recesses 61 may be provided to the locking plate 60 to enhance the position-ability of skull clamp arc assembly 26 relative to the skull clamp 22. With movement of the cam 76 to engage the locking lever 88, the locking lever 88 contracts a biasing spring 98 and engages a recess 96 in the locking pin 84. As the cam 76 continues to move, the locking lever 88, via its engagement with the recess 96, retracts the locking pin 84 from the recess 61, thereby contracting the biasing spring 98 there-under. Retraction of the locking pin 84 unlocks the rocker guide assembly 68 and permits rotation thereof relative to the locking plate 60 and about the axis 40. An indicator 100 may be configured to project from the body 62 of the lower rocker assembly 68 to indicate an unlocked status of the rocker guide assembly 68 and its potential to rotate.

In addition, the rocker assembly guide 68 may be operable such that, with pivoting of the lower rocker assembly 70 about the first pivot point 66A other than to the maximum pivot away from the axis 40, the cam 76 is disengaged from the locking lever 88. Thus, the spring 98 biases the locking pin 84 toward the locking plate 60 so that it inserts into a recess 61 in the locking plate 60. Thereby, the locking pin 84 maintains a locked state so that the skull clamp arc assembly 26 is not rotatable relative to the locking plate 60 and the first or second end 30A, 30B from which the assembly 26 extends. More particularly, with movement of the cam 76 to disengage the locking lever 88, the biasing spring 98 is free to expand to its relaxed state to transition the locking lever 88 and the locking pin 84 from the retracted state into the recess 61 to the locked state so as to prevent the rocker guide assembly 68 from rotating.

Figure 2:
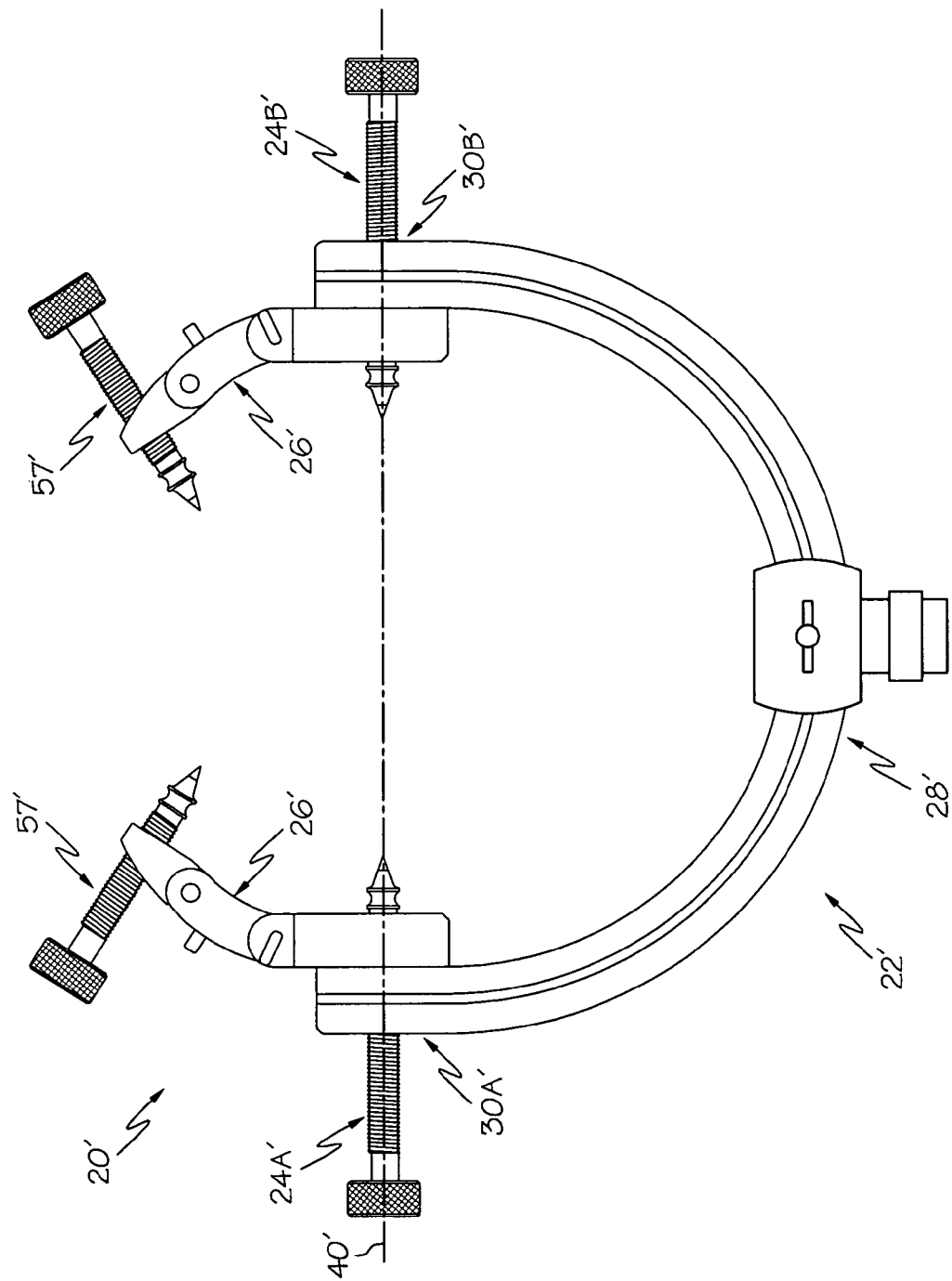
FIG. 2 illustrates a frontal view of a head fixation device according to another embodiment of the present disclosure.
Figure 8:
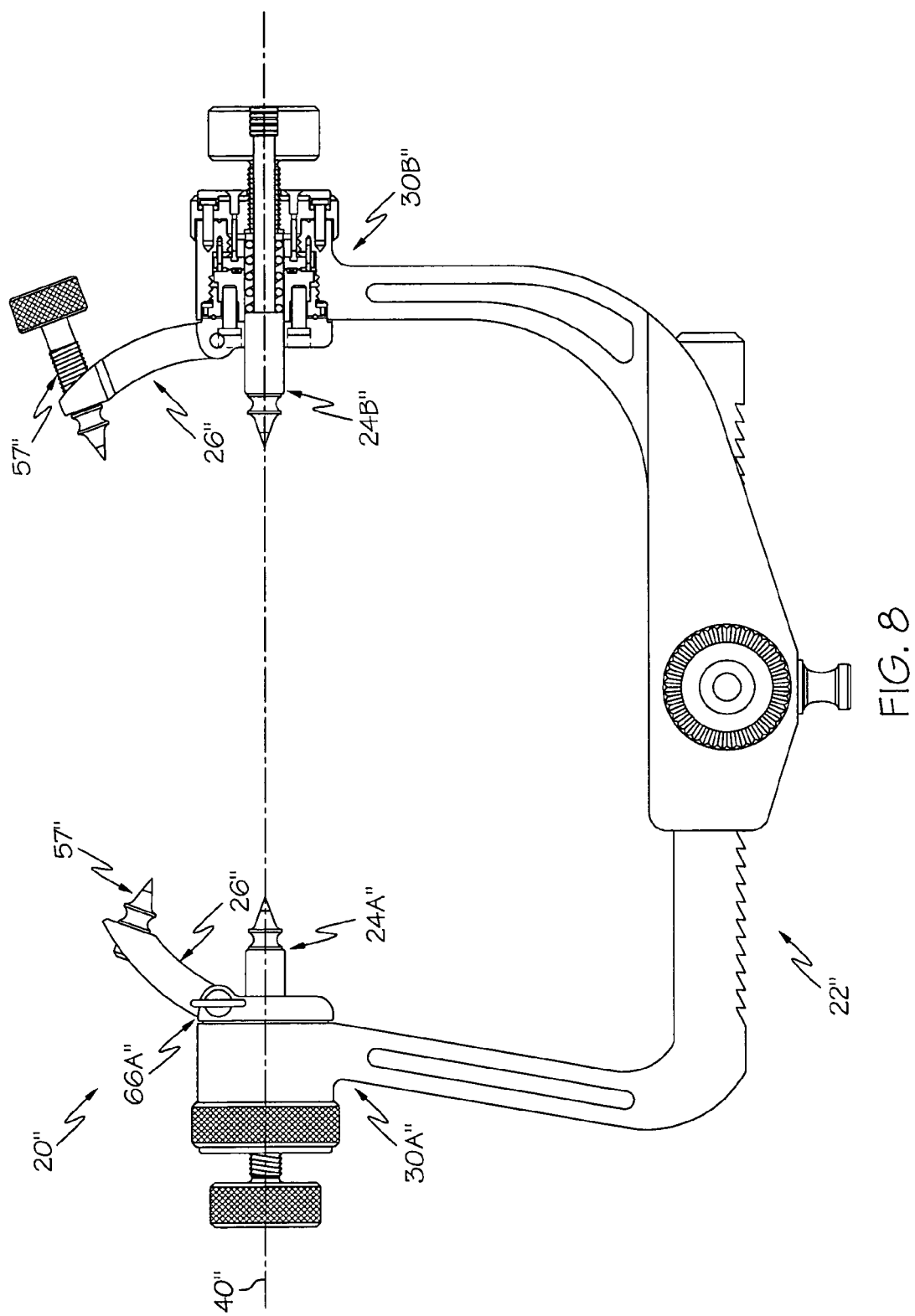
FIG. 8 illustrates a frontal view of a head fixation device according to another embodiment of the present disclosure.

Additional embodiments of the head fixation device are shown in FIGS. 2 and 8. FIG. 2 illustrates a head fixation device 20' comprising a skull clamp 22', two skull pins 24A', 24B' movable relative to the skull clamp 22', and two skull clamp arc assemblies 26', respectively comprising an arc skull pin 57', that extend from the first and second ends 30A', 30B' and are movable relative to the skull clamp 22' and the axis 40' along which the two skull pins 24A', 24B' are aligned in opposition. Further, the skull clamp 22' comprises a body 28' having a more curved configuration that is absent a ratcheting mechanism 36. Rather, the first and second skull pins 24A', 24B' respectively are operable to move laterally and independently of the first and second ends 30A', 30B', as described in greater detail below, so as to adjust the length of the gap 32 separating the first and second skull pins 24A', 24B'.

Figure 10A:
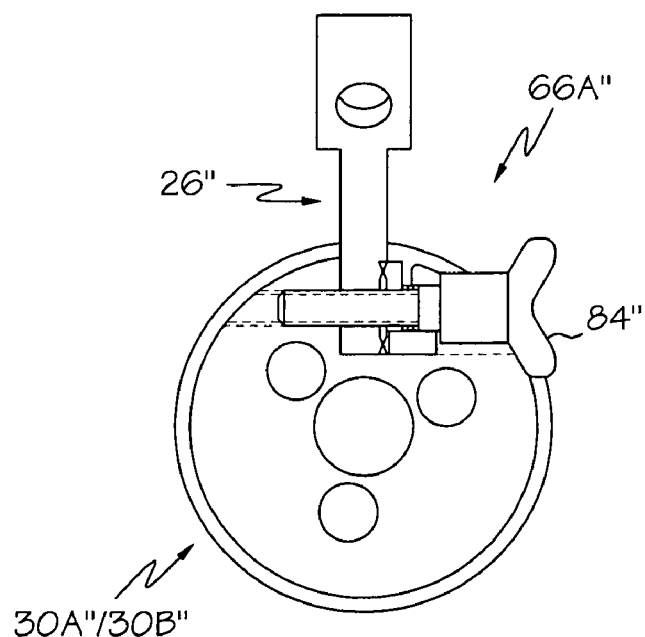
FIG. 10A illustrates a frontal view of a skull clamp arc assembly of a head fixation device according to another embodiment of the present disclosure.
Figure 10B:
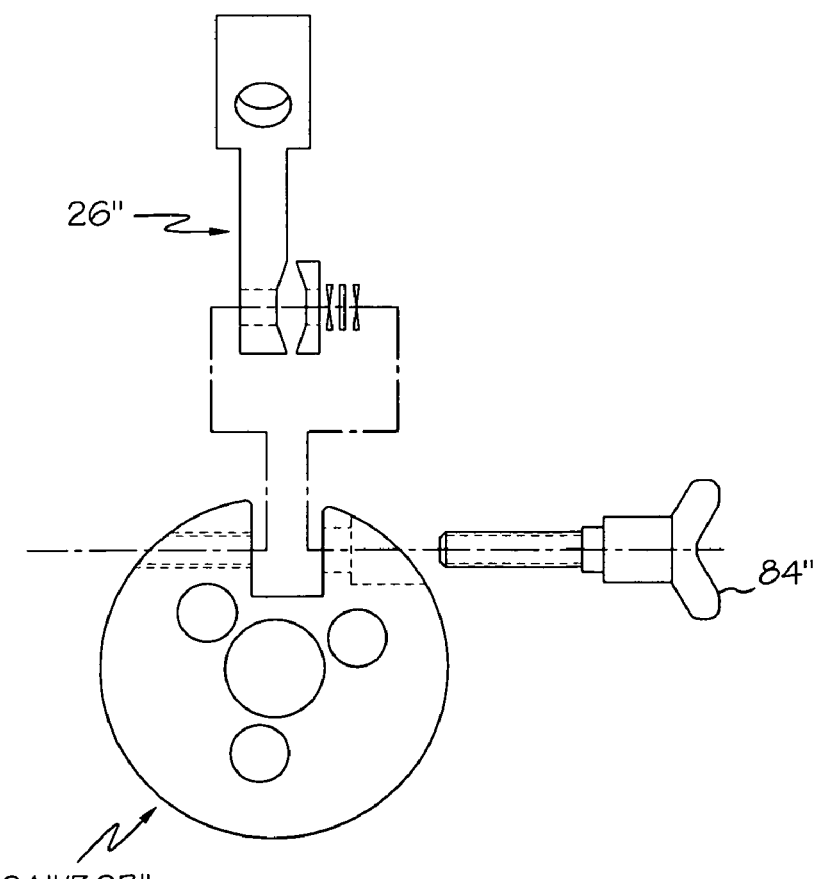
FIG. 10B illustrates an exploded view of the skull clamp arc assembly of the head fixation device illustrated in FIG. 10A.

FIG. 8 illustrates another embodiment of a head fixation device 20" comprising a skull clamp 22", two skull pins 24A", 24B" movable relative to the skull clamp 22", and two skull clamp arc assemblies 26", respectively comprising an arc skull pin 57", that extend from the first and second ends 30A", 30B" and are movable relative to the skull clamp 22" and the axis 40" along which the two skull pins 24A", 24B" are aligned. The skull clamp arc assemblies 26" are illustrated as respectively comprising only the first pivot point 66A", rather than both the first and second pivot points 66A, 66B described herein. In addition, as shown in FIG. 10, the assembly 26" may comprise a locking pin 84" operable to preclude and permit movement of the assembly 26" about the pivot point 66A". Thus, while the disclosure provided herein generally is specific to one skull arc assembly 26 extending from one of the first and second ends 30A, 30B of the skull clamp 22, as shown in FIG. 1, it is contemplated that an embodiment of the head fixation device of the present disclosure, such as, but not limited to those shown in FIGS. 2 and 8, further may comprises a second skull arc assembly 26 that may be configured and operable in the same as that described herein or inferable there-from.

Further additional embodiments of the present disclosure relate generally to methods of fixating heads of patients using embodiments of the head fixation devices of the present disclosure. For example, in one embodiment, a method of fixating a head of a patient comprises providing a head fixation device operable to fixate the head of the patient. The head fixation device comprises: a skull clamp comprising a first end and a second end opposing the first end, a first skull pin provided to the first end of the skull clamp and a second skull pin provided to the second end of the skull clamp, wherein the first and second skull pins are aligned in opposition along a axis, and a skull clamp arc assembly comprising an arc skull pin, wherein the skull clamp arc assembly extends from one of the first and second ends of the skull clamp such that the arc skull pin is offset from the axis and the first and second skull pins aligned thereon. The head fixation device is them positioned about the head of the patient such that the first and second ends of the skull clamp are positioned about the head of the patient. Thereafter, at least one of the first and second skull pins are moved relative to the first and second ends of the skull clamp such that the first and second skull pins engage the first and second sides of the head of the patient and the skull clamp arc assembly is rotated relative to the one of the first and second ends from which the skull clamp arc assembly extends such that the skull clamp arc assembly rotates about the axis to selectively position the arc skull pin over a third side of the head of the patient. Further, the skull clamp arc assembly is pivoted relative to the one of the first and second ends from which the skull clamp arc assembly extends such that the arc skull pin pivots to engage the third side of the head of the patient. Engagements of the first, second, and third sides of the head of the patient by the first skull pin, the second skull pin, and the arc skull pin, respectively, sufficiently fixate the head of the patient.

It is contemplated that embodiments of the head fixation device of the present disclosure further may comprise one or more components operable, individually or in combination, to connect and/or secure the skull clamp of the head fixation device to a surgical table or gurney. Such components may include, but are not limited to, table clamps, rail clamps, and extension supports, that may attach, directly or indirectly, to the skull clamp.

Further, it is noted that recitations herein of a component of an embodiment being "configured" in a particular way or to embody a particular property, or function in a particular manner, are structural recitations as opposed to recitations of intended use. More specifically, the references herein to the manner in which a component is "configured" denotes an existing physical condition of the component and, as such, is to be taken as a definite recitation of the structural factors of the component.

It is noted that terms like "generally," "commonly," and "typically," when utilized herein, are not utilized to limit the scope of the claimed embodiments or to imply that certain features are critical, essential, or even important to the structure or function of the claimed embodiments. Rather, these terms are merely intended to identify particular aspects of an embodiment or to emphasize alternative or additional features that may or may not be utilized in a particular embodiment.

For the purposes of describing and defining embodiments herein it is noted that the terms "substantially," "significantly," and "approximately" are utilized herein to represent the inherent degree of uncertainty that may be attributed to any quantitative comparison, value, measurement, or other representation. The terms "substantially," "significantly," and "approximately" are also utilized herein to represent the degree by which a quantitative representation may vary from a stated reference without resulting in a change in the basic function of the subject matter at issue.

Having described embodiments of the present disclosure in detail, and by reference to specific embodiments thereof, it will be apparent that modifications and variations are possible without departing from the scope of the embodiments defined in the appended claims. More specifically, although some aspects of embodiments of the present disclosure are identified herein as preferred or particularly advantageous, it is contemplated that the embodiments of the present disclosure are not necessarily limited to these preferred aspects.

What is claimed is:

1. A head fixation device comprising: a skull clamp positionable about a head of a patient, wherein the skull clamp comprises a first end and a second end opposing the first end; a first skull pin provided to the first end of the skull clamp and a second skull pin provided to the second end of the skull clamp, wherein the first and second skull pins are aligned in opposition along a first axis, and wherein at least one of the first and second skull pins is movable axially relative to the first and second ends such that the first and second skull pins engage and disengage the head of the patient when the skull clamp is positioned thereabout; and a skull clamp arc assembly comprising an arc skull pin, wherein the skull clamp arc assembly extends rotatably from the first end of the skull clamp, wherein the first skull pin extends through the first end of the skull clamp and through the skull clamp arc assembly along the first axis, wherein the skull clamp arc assembly rotates about the first skull pin, wherein the arc skull pin is offset from the first axis, and wherein the arc skull pin is pivotable relative to the first end of the skull clamp to engage and disengage the head of the patient.

2. The head fixation device of claim 1, wherein the skull clamp arc assembly includes one or more pivot points that are pivotable relative to the first and second ends, such that the arc skull pin pivots toward and away from the first axis so as to engage and disengage the head of the patient when the skull clamp is positioned thereabout.

3. The head fixation device of claim 2, wherein the skull clamp arc assembly comprises: a rocker guide assembly securable to the one of the first and second ends from which the skull clamp arc assembly extends; a lower rocker assembly securable to the rocker guide assembly at a first pivot point and pivotable about the first pivot point toward and away from the first axis; and an upper rocker assembly securable to the lower rocker assembly at a second pivot point and pivotable about the second pivot point toward and away from the first axis, and wherein the upper rocker assembly comprises an upper rocker arc operable to receive and support the arc skull pin, wherein the arc skull pin engages and disengages the head of the patient with pivoting of the upper rocker arc about the second pivot point toward and away from, respectively, the first axis.

4. The head fixation device of claim 3, wherein the lower rocker arm assembly comprises a lower rocker arc that is pivotable about the first pivot point, and a pawl lever that is movable between an unlocked state in which the upper rocker assembly is pivotable about the second pivot point and a locked state in which the upper rocker assembly is not pivotable about the second pivot point.

5. The head fixation device of claim 2, wherein the skull clamp arc assembly is rotatable relative to the first and second ends such that the skull clamp arc assembly rotates about the first axis with pivoting of the arc skull pin about at least one of the plurality of pivot points to a maximum pivot away from the first axis.

6. The head fixation device according to claim 1, wherein the skull clamp arc assembly further comprises a rocker guide assembly rotatably secured to the first end of the skull clamp and between the first end and the second end of the skull clamp, the first skull pin extending through the rocker guide assembly, wherein the rocker guide assembly is rotatable around the first axis, and a rocker assembly securable to and extending from the rocker guide assembly at a pivot point, wherein the rocker assembly pivots about the pivot point toward and away from the first axis, wherein the arc skull pin extends from a distal end of the rocker assembly and is offset from the first axis, the arc skull pin being pivotable with the rocker assembly toward and away from the first axis.

7. The head fixation device of claim 6, wherein the arc skull pin is movable threadedly through the distal end of the rocker assembly.

8. The head fixation device according to claim 6, wherein the rocker assembly is pivotably about the pivot point in a plane through the first axis, and toward and away from the first axis, and wherein the arc skull pin is pivotable with the rocker assembly in the plane through the first axis, toward and away from the first axis.

9. The head fixation device according to claim 6 wherein the arc skull pin is threaded through the distal end of the skull clamp arc assembly.

10. The head fixation device of claim 6, wherein the rocker guide assembly comprises a body, a locking pin, a recess in the body at least partially housing the locking pin, a locking lever engaged with the locking pin, a cam movable to engage and disengage the locking lever, and a channel through the body through which the rocker guide assembly is securable to the one of the first and second ends of the skull clamp.

11. The head fixation device of claim 1, wherein: the one of the first and second ends of the skull clamp from which the skull clamp arc assembly extends comprises a locking assembly operable to secure the skull clamp arc assembly to the one of the first and second ends, and the locking assembly comprises a locking plate, an o-ring, and a snap ring.

12. The head fixation device of claim 11, wherein: the locking plate is operable to secure to the one of the first and second ends of the skull clamp from which the skull clamp arc assembly extends and to support the skull clamp arc assembly and comprises a post and a depression provided proximally to an end of the post, the o-ring is positionable about the post of the locking plate and is operable to facilitate movement of the skull clamp arc assembly relative to the locking plate, and the snap ring is operable to secure to the depression of the locking plate and secure the skull clamp arc assembly to the post of the locking plate.

13. The head fixation device of claim 1, wherein the first skull pin, the second skull pin, and the arc skull pin, respectively, comprise a tip operable to engage and disengage the head of the patient when the skull clamp is positioned thereabout, a plunger operable to support the tip, a plunger guide operable to control movement of the plunger and the tip, a compression spring operable to translate movement of the plunger guide to the plunger and the tip, and an indicator operable to indicate a compressive force provided by the tip against the head of the patient when the skull clamp is positioned thereabout.

14. The head fixation device of claim 1, wherein the head fixation device comprises multiple skull clamp arc assemblies that extend from the first and second ends of the skull clamp.

15. The head fixation device according to claim 1 wherein the arc skull pin includes a compressive force indicator operable to indicate the compressive force of the arc skull pin.

16. The head fixation device according to claim 1 wherein the arc skull pin includes a knob for rotating, a compressible pressure spring that exerts a force on a plunger in response to rotation of the knob, and a tip disposed at the distal end of the plunger for placement against and applying compressive force against the skull of the patient.

17. The head fixation device according to claim 1, wherein the first end of the skull clamp from which the skull clamp arc assembly extends, comprises a locking assembly for securing the skull clamp arc assembly from rotation.

18. The head fixation device according to claim 1, wherein the skull clamp can rotate independently of the skull clamp arc assembly and the first and second skull pins.

* * * * *